US012329885B2

United States Patent
Grüebler et al.

(10) Patent No.: US 12,329,885 B2
(45) Date of Patent: Jun. 17, 2025

(54) ENHANCED STIFFENING IMPLEMENT FOR A SURGICAL TOOL

(71) Applicant: Alcon Inc., Fribourg (CH)

(72) Inventors: Reto Grüebler, Greifensee (CH); Bernhard Pultar, Winterthur (CH); Klaus Dorawa, Kiel (DE)

(73) Assignee: Alcon Inc., Fribourg (CH)

( * ) Notice: Subject to any disclaimer, the term of this patent is extended or adjusted under 35 U.S.C. 154(b) by 504 days.

(21) Appl. No.: 17/644,186

(22) Filed: Dec. 14, 2021

(65) Prior Publication Data

US 2022/0193311 A1 Jun. 23, 2022

Related U.S. Application Data

(60) Provisional application No. 63/126,710, filed on Dec. 17, 2020.

(51) Int. Cl.
| | |
|---|---|
| *A61F 9/007* | (2006.01) |
| *A61F 9/013* | (2006.01) |
| *A61L 31/08* | (2006.01) |
| *A61L 31/14* | (2006.01) |
| *A61B 17/28* | (2006.01) |

(52) U.S. Cl.
CPC .......... *A61L 31/14* (2013.01); *A61F 9/00736* (2013.01); *A61F 9/013* (2013.01); *A61L 31/088* (2013.01); *A61B 17/28* (2013.01); *A61L 2420/02* (2013.01); *A61L 2420/06* (2013.01)

(58) Field of Classification Search
CPC .... A61L 31/14; A61L 31/088; A61L 2420/02; A61L 2420/06; A61F 9/00736; A61F 9/013; A61B 17/28
See application file for complete search history.

(56) References Cited

U.S. PATENT DOCUMENTS

| | | | |
|---|---|---|---|
| 6,488,695 | B1 | 12/2002 | Hickingbotham |
| 6,926,965 | B2 | 8/2005 | Qiu et al. |
| 7,662,170 | B2 | 2/2010 | Mashiko et al. |
| 8,202,277 | B2 | 6/2012 | Ryan |
| 8,308,737 | B2 | 11/2012 | Ryan |
| 9,060,841 | B2 | 6/2015 | Mccawley |
| 9,931,244 | B2 | 4/2018 | Ryan |
| 9,956,053 | B2 | 5/2018 | Diao |
| 10,864,001 | B2 | 12/2020 | Vezzu |
| 10,898,373 | B2 | 1/2021 | Ryan |

(Continued)

FOREIGN PATENT DOCUMENTS

| | | |
|---|---|---|
| WO | 2020004667 A1 | 1/2020 |
| WO | WO-2021113361 A1 * | 6/2021 ........... A61B 17/068 |

*Primary Examiner* — Ankit D Tejani
*Assistant Examiner* — Joshua Brendon Solomon
(74) *Attorney, Agent, or Firm* — PATTERSON + SHERIDAN, LLP

(57) ABSTRACT

A surgical tool with an elongated implement of enhanced stiffening character due to the use of a stiffening coating and/or a lumen of inconsistent diameter. The stiffening coating may be supplied by a deposition technique utilizing materials tailored to biocompatibility, stiffening and even to reducing glare. The lumen of inconsistent diameter may include a distal end taking up a minority of the lumen that is of a larger diameter than a proximal portion of substantially smaller diameter for increasing wall thickness and stiffening of the majority of the implement.

9 Claims, 6 Drawing Sheets

(56) References Cited

U.S. PATENT DOCUMENTS

| | | |
|---|---|---|
| 11,224,539 B2 | 1/2022 | Grueebler |
| 2002/0142182 A1 | 10/2002 | Peker et al. |
| 2005/0059939 A1 | 3/2005 | Perkins et al. |
| 2006/0058843 A1* | 3/2006 | Mashiko ............ A61C 5/42 606/222 |
| 2008/0033462 A1* | 2/2008 | Di Nardo ........... A61F 9/007 606/166 |
| 2013/0035551 A1 | 2/2013 | Yu |
| 2013/0053759 A1 | 2/2013 | Mccawley |
| 2015/0173944 A1 | 6/2015 | Linsi |
| 2015/0313755 A1 | 11/2015 | Schaller |
| 2016/0296246 A1 | 10/2016 | Schaller |
| 2019/0216645 A1* | 7/2019 | Klufas ............ A61F 9/0079 |
| 2020/0187970 A1* | 6/2020 | Abt ............... A61B 17/2909 |
| 2020/0188022 A1* | 6/2020 | Mingione ......... A61B 18/1815 |
| 2020/0309760 A1* | 10/2020 | Durant ............ G01N 27/028 |
| 2021/0059702 A1 | 3/2021 | Abt et al. |
| 2023/0000487 A1* | 1/2023 | Clay ............... A61B 17/068 |

* cited by examiner

ENHANCED STIFFENING IMPLEMENT FOR A SURGICAL TOOL

PRIORITY CLAIM

This application claims the benefit of priority of U.S. Provisional Patent Application Ser. No. 63/126,710 titled "ENHANCED STIFFENING IMPLEMENT FOR A SURGICAL TOOL," filed on Dec. 17, 2020, whose inventors are Reto Grüebler, Bernhard Pultar and Klaus Dorawa, which is hereby incorporated by reference in its entirety as though fully and completely set forth herein.

BACKGROUND

Over the years, many dramatic advancements in the field of minimally invasive surgical procedures have taken place. Accordingly, natural patient injury and healing times have been dramatically reduced. In the area of eye surgery as an example, previously inaccessible injured or deteriorating tissue may be repaired or directly serviced through minimally invasive procedures. When the eye surgery includes accessing the retina, it is common that a vitrectomy will be included in at least part of the procedure. Vitrectomy is the removal of some or all of the vitreous humor from a patient's eye. In some cases, where the surgery was limited to removal of clouded vitreous humor, the vitrectomy may constitute the majority of the procedure. However, a vitrectomy may accompany surgery to repair a retina, to address a macular pucker or a host of other issues.

In keeping with the example of eye surgery and a vitrectomy, the vitreous humor itself is a clear gel that may be removed by an elongated implement in the form of a needle that is inserted through a pre-placed cannula at the eye. More specifically, a surgical tool in the form of a vitrectomy probe is held by a surgeon at a gripping location with a needle emerging from the tool as described. The needle includes a central channel for removal of the vitreous humor. Further, the cannula provides a structurally supportive conduit strategically located at an offset location at the front of the eye, such as the pars plana. In this way, the probe needle may be guidingly inserted into the eye in a manner that avoids damage to the patient's lens or cornea.

Of course, a variety of other tools with different types of implements may also be used as part of minimally invasive eye surgery. This could include the use of a surgical tool with a non-needle implement such as scissors, forceps, a light or other instrument types. Regardless of the particular implement type, it is generally guided and supported by a cannula and trocar assembly which has been prepositioned at the location of an incision through the pars plana as indicated. Thus, the implement may be securely advanced through to the interior of the eye to perform the surgical procedure.

Over the years, minimally invasive eye surgeries have employed smaller and smaller implements for increasingly precise surgical maneuvers. For example, vitrectomy probe needles that traditionally may have been about 23 gauge are now more commonly about 25 or 27 gauge. This translates to reducing a needle diameter from just under about 0.5 mm to less than about 0.4 mm. Considering that a vitrectomy probe needle is likely a few centimeters in length and hollow, this increasingly thin gauge implement is likely to be quite pliable. For other instruments, a similar pliability issue emerges as the implement size becomes increasingly smaller. Once more, the issue is amplified where the implement accommodates an internal feature of varying or sizable diameter. For example, where the implement accommodates forceps, the interior of the needle will include an inner diameter that is large enough to accommodate the actual forceps at the end. Thus, the needle is not only thin in outer diameter but it may also be large in inner diameter such that the wall of the needle is of substantially reduced thickness making it even more pliable.

Increased pliability or flexibility for a surgical implement is not necessarily helpful to a surgeon during a procedure. Generally speaking, the surgeon is better aided by a degree of rigidity in the implement that affords a greater degree of control. That is, manual manipulation of the implement by the surgeon at an exterior location is more likely to reliably transfer to the surgical site if the implement is more inflexible. So, for example, in the case of a vitrectomy procedure, the probe may include a grip from which the needle extends toward and through the noted cannula structure at the eye. A larger and more rigid stiffening sleeve may extend from the structural support of the cannula and back toward the body and grip of the tool. Thus, at least in the space between the surgeon's grip location and the front of the eye, bending of the needle may be avoided due to the presence of the stiffening sleeve. Rather, a secure and reliably linear translation of movement from the grip to a pivot location at the surface of the eye is displayed (e.g. where the stiffening sleeve contacts the cannula). Once more, the actual length of the needle which presents within the eye and is not structurally bound by the stiffening sleeve is limited. Thus, bending of the needle is further minimized.

Unfortunately, utilizing a stiffening sleeve as detailed, may reduce the effective length of the instrument that can be used inside the eye.

SUMMARY

A surgical tool is described with a body for manual securing by a surgeon during a surgical procedure. The tool includes an implement extending from an end of the body to attain surgical access to a tissue region of a patient for the procedure. In one embodiment, a stiffening coating is provided on an outer surface of the implement for stabilizing the implement during the surgical procedure at the tissue region. In another embodiment, the implement is a tubular implement with a mandrel of a given diameter disposed therein. An actuatable mechanism of another diameter is disposed at a distal end of the mandrel wherein the given diameter is smaller than the other diameter. Thus, the tubular implement includes a first inner diameter about the mandrel that is smaller than a second inner diameter about the mechanism to increase a wall thickness of the tubular implement at the location of the mandrel.

DETAILED DESCRIPTION

In the following description, numerous details are set forth to provide an understanding of the present disclosure. However, it will be understood by those skilled in the art that the embodiments described may be practiced without these particular details. Further, numerous variations or modifications may be employed which remain contemplated by the embodiments as specifically described.

Embodiments are described with reference to certain types of surgical procedures. In particular, an ILM peeling procedure is illustrated wherein the surgical tool includes an implement in the form of forceps. However, tools and techniques detailed herein may be employed in a variety of other manners as well. For example, the implement could be one for scissors, a vitrectomy needle or for supporting any number of other application types. Additionally, while eye surgeries often benefit from the use of fairly thin implements, other types of surgeries may benefit from the unique architecture and techniques detailed herein. Indeed, so long as a stiffening coating or reduced inner diameter architecture is employed for the surgical implement, appreciable benefit may be realized.

Figure 1:
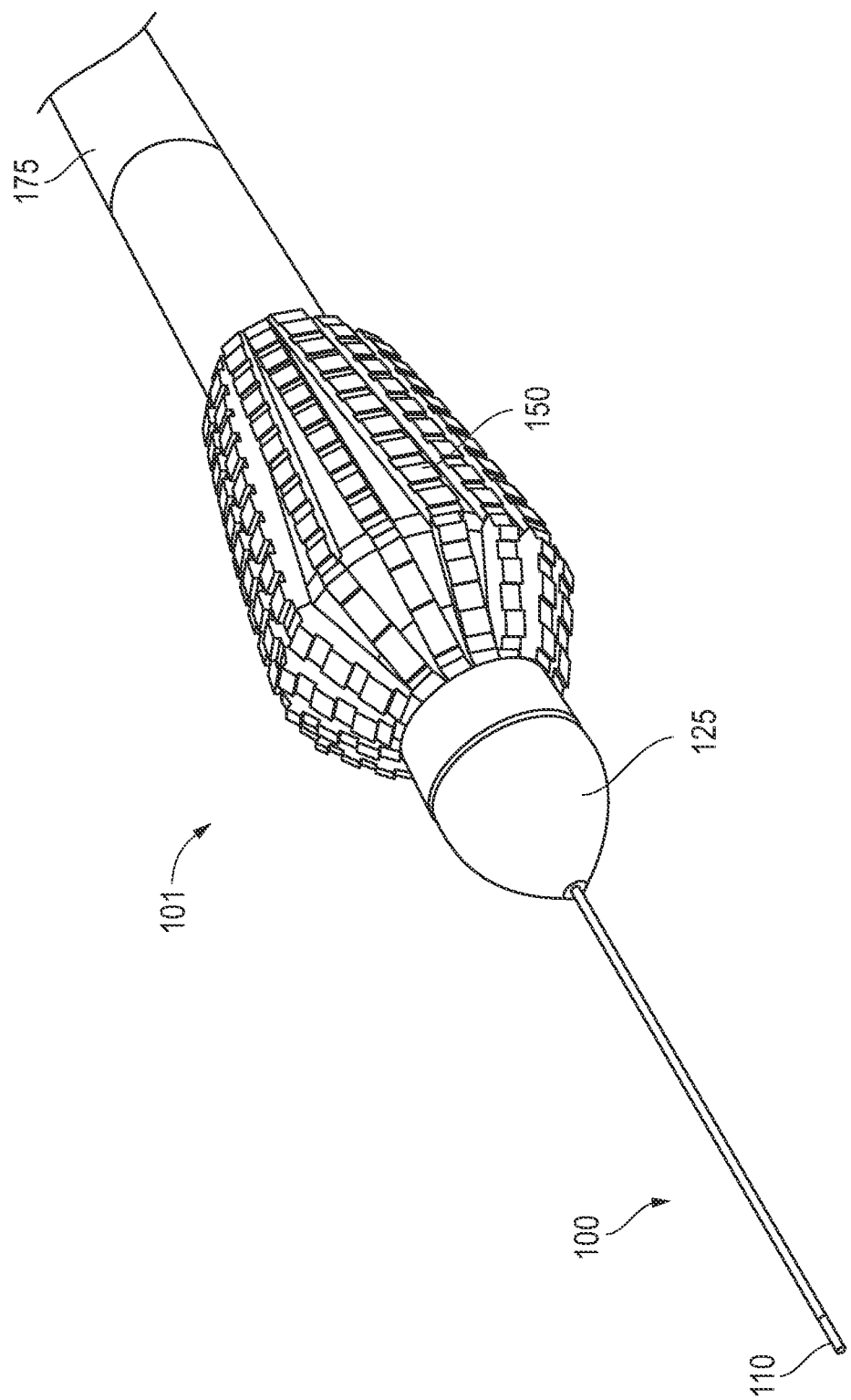
FIG. 1 is a perspective view of a surgical tool for an eye surgery employing an embodiment of an implement of enhanced stiffening character.

Referring now to FIG. 1, a perspective view of a surgical tool 101 for an eye surgery is illustrated. More specifically, the tool 101 utilizes an implement 100 that is of enhanced stiffening character. As detailed further below, the implement 100 includes forceps 110. However, perhaps more notably, the implement 100 is of a unique stiffening character. For example, in one embodiment, the implement 100 includes a 25 gauge or higher stainless steel or other suitable tubular substrate 205 that is covered by a stiffening coating 200 (e.g. see FIGS. 2 and 3). In another embodiment, the implement 100 is of a stiffening architecture with an inner diameter 400, 425 that is intentionally non-uniform. Indeed, a majority 425 of the inner diameter may be reduced for increased stiffening of the implement 100 (e.g. see FIG. 4).

Figure 2:
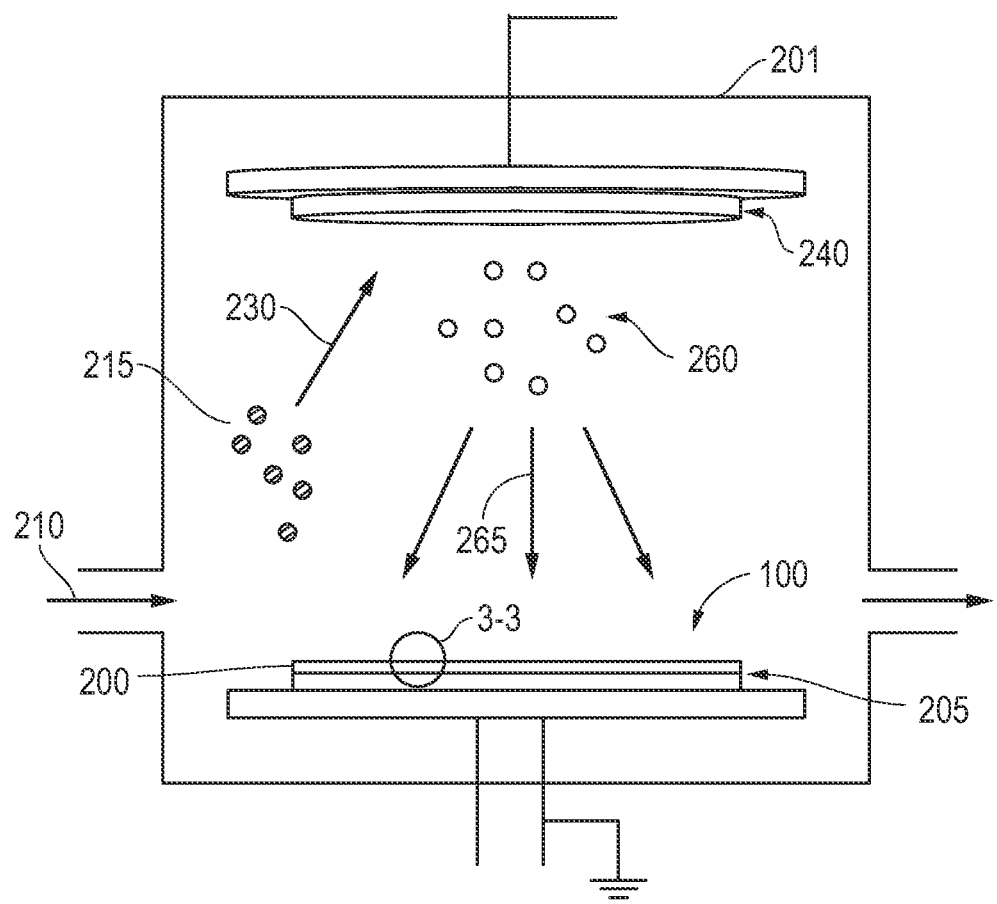
FIG. 2 is a schematic representation of the implement of FIG. 1 positioned within a physical vapor deposition (PVD) chamber to attain the enhanced stiffening character.

Continuing with reference to FIG. 1, with added reference to FIG. 2, the implement 100 may be about 6 cm (centimeters) long and smaller than 25 gauge in diameter sizing as noted. However, a degree of rigidity and stiffness may be added by way of the noted coating 200. In one embodiment, the coating 200 may be anywhere from 1 to 30 microns in thickness (or more) and increase stiffness by anywhere from 5 to 30% (or more). With added reference to FIG. 5, notice that unlike utilizing a stiffening sleeve, the added thickness and stiffening character provided to the implement 100 by the coating 200 is applicable across the entirety of the implement. That is, the stiffness is not limited by the trocar cannula 530 to the exterior of the eye 550 as would be the case for a stiffening sleeve. Rather, the enhanced stiffening supplied by the coating 200 applies across the entirety of the implement 100, including any portion that reaches into the eye 550 for a given procedure.

Referring now to FIG. 2, a schematic representation of the implement 100 of FIG. 1 is shown positioned within a physical vapor deposition (PVD) chamber 201 to attain the enhanced stiffening character. However, in other embodiments, chemical vapor deposition (CVD) or plasma assisted CVD (PACVD) techniques may be utilized, depending on material and other operational parameters. Regardless, for the embodiment illustrated, the implement 100 initially includes a substrate 205 which may be stainless steel or other suitable material for the surgical application that is receptive to a PVD application. That is, the PVD application is tailored to provide an outer coating 200 as referenced above to the substrate 205 to form the implement 100. As suggested above, the coating 200 may be anywhere from about 1-30 microns and of a material selected, at least in part, for enhancing the stiffening character of the implement 100. In the schematic illustration of FIG. 2, the material 260 that ultimately makes up the coating 200, illustrated as sputtered target atoms or molecules, is provided from a solid sputtering target 240 that is biocompatible given the intended use of the implement 100. For example, the target 240 may be a ceramic such as titanium nitride (TiN), aluminum titanium nitride (AlTiN) or titanium niobium nitride (TiNbN), diamond-like carbon (DLC), titanium carbonitride (TiCN) and zirconium nitride (ZrN).

Continuing with reference to FIG. 2, the PVD application proceeds with the circulation of a sputtering gas 210 through a vacuum in the chamber 201. A high temperature vacuum or gaseous plasma 215 is directed at the target 240 (see 230), perhaps at between about 200° C. (degrees Celsius) and 400° C. This generates a vapor that includes the target material 260 which is then available for reaching the substrate 205 to form the coating 200 (see 265). More specifically, this vapor may condensate onto the substrate 205 to form the enhanced implement 100.

Figure 3:
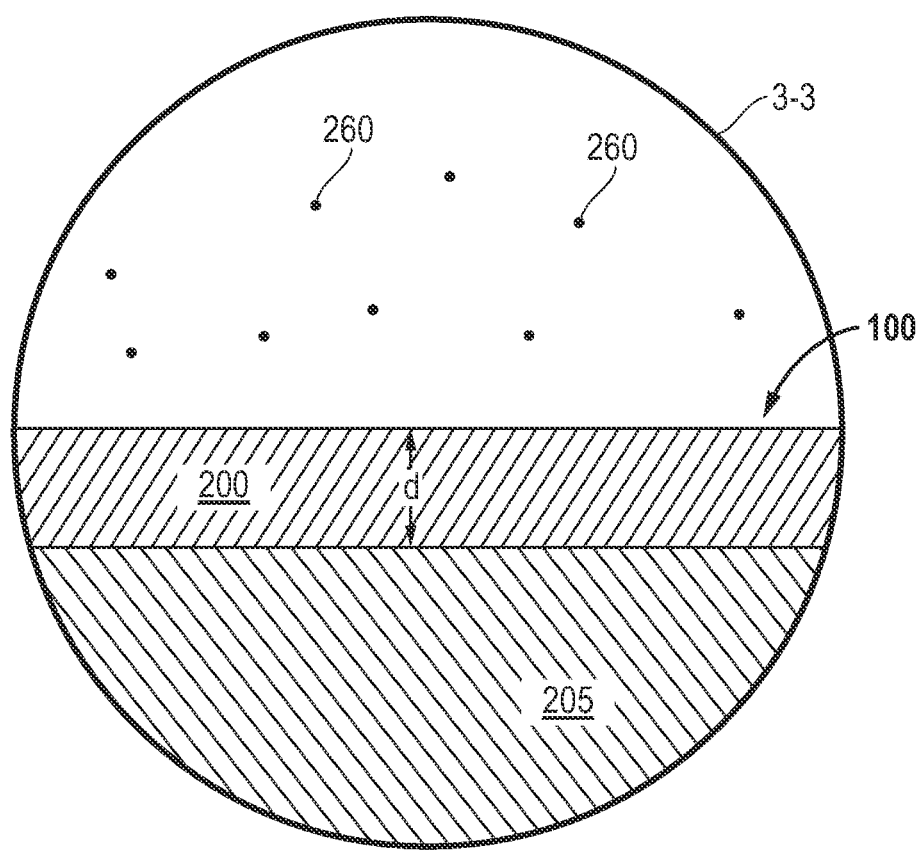
FIG. 3 is an enlarged cross-sectional view of the implement taken from 3-3 of FIG. 2 and illustrating a PVD coating to supply the enhanced stiffening character.

Referring now to FIG. 3, an enlarged cross-sectional view of the implement 100 taken from 3-3 of FIG. 2 is shown. In this illustration, the PVD coating 200 that is attained from the vapor material 260 is readily apparent for supplying the enhanced stiffening character discussed above. More specifically, utilizing the noted types of target materials 260 and providing a coating 200 in the described manner may enhance stiffness by a factor that is substantially greater than the percent thickness added to the implement 100 by the addition of the coating 200. For example, while the coating 200 may constitute less than 10% of the thickness (d) of the entire wall thickness for the implement 100, it may increase stiffening by anywhere from 5% to 30% (or more). By way of a first example, the coating 200 may between 1 to 10 microns thick for a total wall thickness of about 0.06 mm. By way of a second example only, if the implement 100 has an overall wall thickness that is well over about 0.1 inches, the coating 200 may generally constitute less than about 30 microns of that thickness. Nevertheless, stiffening of the implement 100 may be well over 5% as compared to the implement 100 in absence of the coating 200, a factor much greater than the percentage of thickness added by the coating 200. In terms of Young's modulus of elasticity, a metric for stiffness in gigapascals (GPa), the addition of a mere 1 to 30 microns of thickness (d) to the overall thickness may take the stiffness of an underlying steel substrate 205 from 200 GPa up to about 230-250 GPa, a much greater percentage than the percent of thickness added by the coating 200 itself. Other thicknesses and stiffnesses are also contemplated.

Figure 4:
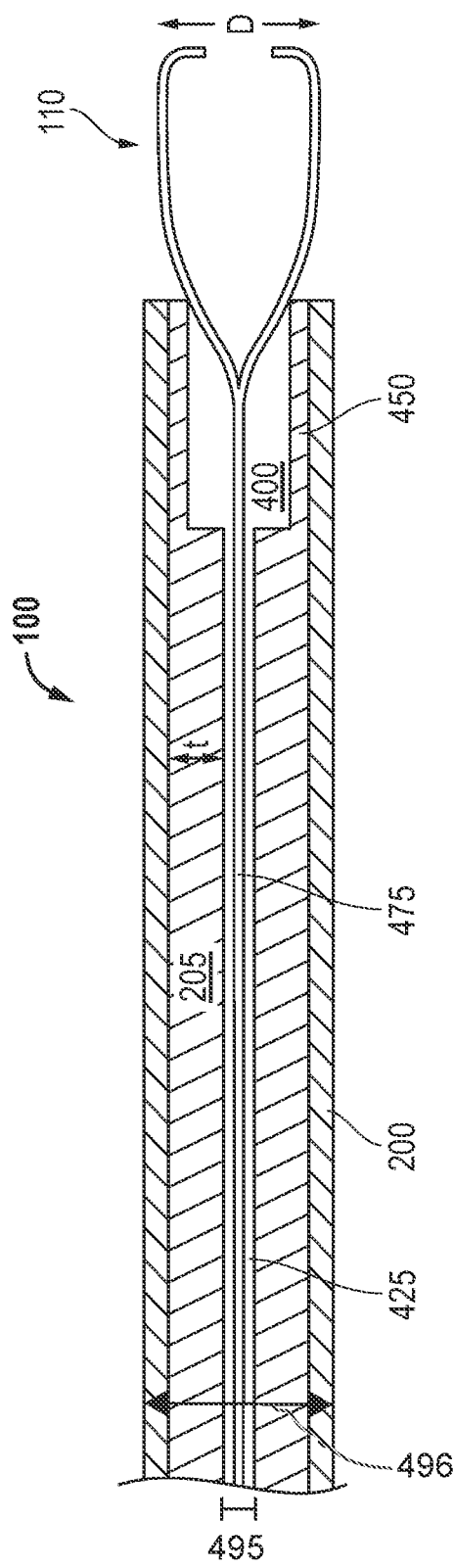
FIG. 4 is a side cross-sectional view of the implement of FIGS. 1-3 illustrating another embodiment of enhanced stiffening character.

Referring now to FIG. 4, a side cross-sectional view of the implement 100 of FIGS. 1-3 illustrating another embodiment of enhanced stiffening character. That is, while the coating 200 is still illustrated for enhanced stiffening, additional stiffening is provided by way of the unique architecture of the underlying substrate 205. More specifically, recall that the substrate 205 is tubular in nature in order to accommodate an internal tool feature. In the embodiment shown, the tool feature constitutes forceps 110. However, in other embodiments, a light instrument, scissors or any number of tool features may be employed with the implement 100.

Continuing with reference to FIG. 4, as with many other tool features, the forceps 110 are of an irregular diameter. More specifically, the forceps 110 reach a maximum outer diameter (D) which may closely match that of a tool chamber 400 within the implement substrate 205. In the embodiment shown, the forceps 110 may even reach a maximum outer diameter (D) that is slightly larger than that of the chamber 400 but also be collapsible thereinto. Regardless, in the embodiment shown, the chamber 400 is the only portion of the substrate 205 that is sized to accommodate the forceps 110. This is because the remainder of the tool feature is limited to the diameter of a wire or "mandrel" 475 that accommodates the forceps 110 at the distal end thereof. As a result, a smaller proximal diameter 425 may run the majority of the tubular interior or lumen of the substrate 205.

As a practical matter, this means that the wall thickness (t) of the majority of the substrate 205 will be substantially greater than at the chamber location. That is, there is no requirement that the entirety of the tubular interior of the substrate 205 be of a diameter to accommodate the forceps 110. Instead, a substantially greater wall thickness (t) may be utilized to provide even greater enhanced stiffening throughout the majority of the implement 100. Indeed, only the distal end 450 of the substrate 205 that defines the chamber 400 will be lacking in this type of enhanced stiffening. However, note that in the embodiment shown, enhanced stiffing is still supplied by the coating 200 even at the distal end 450.

By way of exemplary illustration only, the proximal diameter 495 may be about 0.25 mm for a 27 Gauge instrument and about 0.3 mm for a 25 Gauge instrument. In some embodiments, the chamber diameter (of chamber 400) is about 0.35 mm for a 27 Gauge instrument and about 0.37 mm for a 25 Gauge instrument. Correspondingly, the wall thickness (t) throughout the majority of the substrate 205 may be greater than 0.25 mm. The structure is tubular in nature which means that the diameter 496 of the entire shaft of the tool may be about 0.52 mm for a 25 Gauge instrument and about 0.42 mm for a 27 gauge instrument (this diameter 496 may include the added thickness supplied by the coating 200). While example dimensions have been provided above for the proximal diameter 495, chamber diameter of chamber 400, and diameter 496 of the entire shaft, it is to be understood that other diameters for these components (larger or smaller) may be used for 25, 27, or other gauge instruments.

Regardless of the particular dimensions, employing a lumen where the majority includes a substantially smaller proximal diameter 475 than at the distal end 450, means that substantial stiffening enhancement may be obtained for the implement 100. Indeed, even in absence of the illustrated coating 200, a stiffening increase of anywhere between about 5% and about 30% (or more) may still be expected. Again, in terms of metrics, a steel substrate 205 may reach an increased stiffening of up to about 230-250 GPa throughout the majority, even without the coating 200, as compared to a GPa of 200 or less where the proximal diameter 475 is equal to that of the chamber 400. Once more, for the embodiment illustrated where both the added thickness (t) and the coating 200 are employed, the stiffening may be increased to over 250 GPa (and/or beyond 30%).

Figure 5:
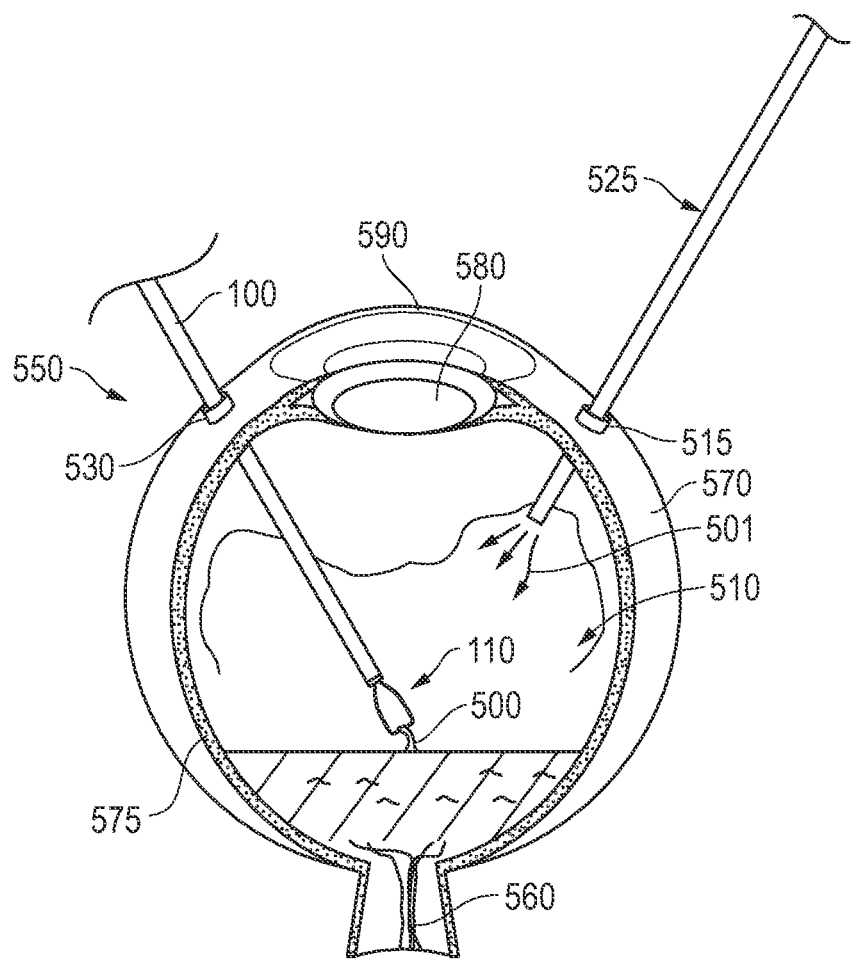
FIG. 5 is an overview depiction of an internal limiting membrane (ILM) surgical procedure employing the tool of FIG. 1 with an implement of enhanced stiffening character.

Referring now to FIG. 5, an overview depiction of an internal limiting membrane (ILM) surgical procedure is illustrated. Specifically, the procedure employs the tool 101 of FIG. 1 with an implement 100 of enhanced stiffening character. In this view, the implement 100 of FIG. 1, with forceps 110, is utilized. During this surgical procedure, the implement 100 is inserted through a preplaced cannula 530 and directed toward a region 510 where an ILM 500 is to be peeled. For example, this may be a procedure undertaken to help avoid macular hole formation or a variety of other issues often associated with the ILM.

The surgery illustrated also includes the positioning of a light instrument 525 reaching into the eye 550 through another cannula 515 that is positioned in an offset manner at the sclera 570. Indeed, both cannulas 515, 530 are shown positioned in such an offset manner. Thus, damage to the more delicate cornea 590 and lens 580 may be avoided.

Of course, the optic nerve 560, retina 575 and other portions of the eye 550 are also quite delicate. Therefore, employing an implement 100 of enhanced stiffening character may be of substantial benefit. That is, rather than relying on an implement that is more prone to elasticity and bending, unique techniques and architecture may be employed to enhance the stiffening character of the implement 100. As a result, the surgeon may be afforded a greater degree of control over the entirety of the implement 100 during the procedure. Thus, the odds of successful surgery may be improved. Indeed, while the embodiments focused on herein are directed at enhanced stiffening character for a forceps implement 100, the same techniques and architecture may be applied to the light instrument 525 or a variety of other implement types. Once more, unlike a conventional stiffening sleeve, enhancing stiffening character of the implement 100 through techniques and architecture detailed herein, includes enhancing stiffening for portion of the implement 100 that reaches into the eye 550 during the illustrated procedure.

Continuing with added reference to FIGS. 2 and 3, it is of note that where the coating 200 is supplementally provided as discussed, the material 260 selected may be chosen to minimize glare during the above-described procedure. For example, given that light 501 is provided from an adjacent instrument 525, the possibility of generating an unhelpful glare at the surface of the implement 100 exists. Thus, the opportunity to minimize glare is afforded where the appropriate material 260 is selected for the coating 200. In this regard, by way of comparison to stainless steel, DLC, TiN, and/or TiCN based materials may be utilized which are prone to less glare. Indeed, the particular coating composition utilized may be selected and tailored to decrease glare. Employing such techniques should afford a decrease in glare by up to 50% as compared to a conventional exposed stainless steel implement.

Figure 6:
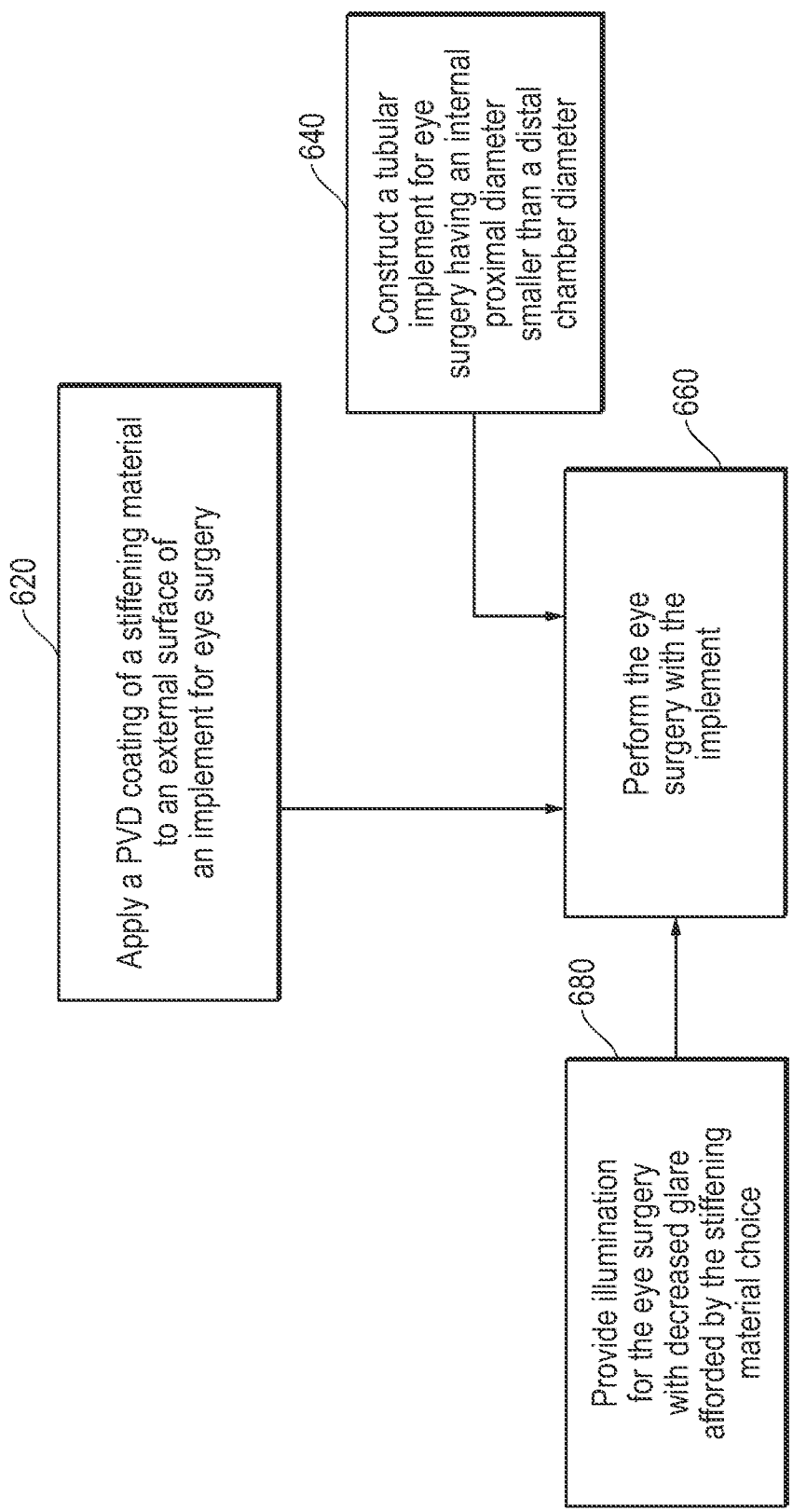
FIG. 6 is a flow-chart summarizing an embodiment of employing a surgical tool with an implement of enhanced stiffening character in an eye surgery.

Referring now to FIG. 6, a flow-chart summarizing an embodiment of employing a surgical tool with an implement of enhanced stiffening character in an eye surgery is shown. As noted at 620 and 640, respectively, enhanced stiffening character may be attained either through application of a PVD coating with a stiffening material or through the construction of an implement with a proximal diameter smaller than a distal chamber diameter. Of course, both concepts may be utilized within the same implement. Regardless, an eye surgery may be performed with the implement as indicated at 660. Further, where the enhanced stiffening includes the application of the PVD coating, the material choice may support decreased glare for the surgery.

Embodiments described hereinabove include techniques and architecture that allow for the avoidance of a stiffening sleeve to compensate for bending tendencies as eye surgical implements become smaller and smaller. Thus, the limitations presented by stiffening sleeves may be avoided or at least not solely relied upon to enhance stiffening. Once more, the stiffening enhancement may traverse a majority of, or the entirety of the implement, including portions within the eye during surgery. In one embodiment, a reduction in glare may even be attained through use of select stiffening material choices.

The preceding description has been presented with reference to specific embodiments. However, other embodiments and/or features of the embodiments disclosed but not detailed hereinabove may be employed. Furthermore, persons skilled in the art and technology to which these embodiments pertain will appreciate that still other alterations and changes in the described structures and methods of operation may be practiced without meaningfully departing from the principle and scope of these embodiments. Additionally, the foregoing description should not be read as pertaining only to the precise structures described and shown in the accompanying drawings, but rather should be read as consistent with and as support for the following claims, which are to have their fullest and fairest scope.

The invention claimed is:

1. A surgical tool, comprising:
   a tool body for manual securing by a surgeon for a surgical procedure;
   a surgical implement extending from an end of the body to attain surgical access to a tissue region of a patient for the procedure; and
   a stiffening coating on an outer surface of the implement for stabilizing the implement during the surgical procedure at the tissue region, wherein:
      the coating is between about 1 micron and 30 microns in thickness to increase stiffness by between about 5% and about 30%; and
      the implement is tubular with a distal chamber diameter to accommodate a tool feature and a proximal inner diameter that is substantially smaller than the distal chamber diameter, the proximal inner diameter occupying a majority of the tubular implement inner diameter to further enhance stiffening of the majority of the implement by more than 30%.

2. The surgical tool of claim 1, wherein the tool includes one of forceps, scissors, a vitrectomy needle and a light instrument.

3. The surgical tool of claim 1, wherein the stiffening coating is one of a physical vapor deposition (PVD) coating, a chemical vapor deposition (CVD) coating, and a plasma assisted CVD (PACVD) coating.

4. The surgical tool of claim 3, wherein the coating is of a material selected from a group consisting of titanium nitride, aluminum titanium nitride, titanium niobium nitride, diamond-like carbon, titanium carbonitride and zirconium nitride.

5. The surgical tool of claim 4, wherein the stiffening coating material selected is tailored to decrease glare during the surgical procedure.

6. A surgical tool, comprising:
   a tool body for manual securing by a surgeon for a surgical procedure;
   a tubular implement extending from an end of the body to attain surgical access to a tissue region of a patient for the procedure;
   a mandrel of a given diameter within the tubular implement, wherein the mandrel is a wire supporting an actuatable mechanism; and
   the actuatable mechanism of another diameter at a distal end of the mandrel, the given diameter smaller than the other diameter and the tubular implement having a first inner diameter about the mandrel and a second inner diameter about the mechanism, the first diameter smaller than the second to increase a wall thickness of the tubular implement thereat.

7. The surgical tool of claim 6, wherein the smaller first diameter is less than about 0.25 mm (millimeters) and the larger second diameter is greater than about 0.35 mm.

8. The surgical tool of claim 6, wherein the actuatable mechanism is forceps.

9. The surgical tool of claim 6, further comprising one of a PVD delivered stiffening coating, a CVD stiffening coating and a PACVD stiffening coating on an outer surface of the tubular implement for further stiffening the implement.

* * * * *